US005772059A

United States Patent [19]
McCord

[11] Patent Number: 5,772,059
[45] Date of Patent: Jun. 30, 1998

[54] CLOSURE FOR SHARPS DISPOSAL CONTAINER HAVING TEMPORARY AND PERMANENT CLOSED POSITIONS

[75] Inventor: Kenneth R. McCord, Encinitas, Calif.

[73] Assignee: Med-Safe Systems, Inc., Oceanside, Calif.

[21] Appl. No.: 792,770

[22] Filed: Feb. 3, 1997

[51] Int. Cl.$^6$ .................................................. B65D 51/18
[52] U.S. Cl. .................... 220/254; 220/324; 220/338; 220/334; 220/906; 220/315; 215/230
[58] Field of Search ..................... 215/206, 230, 215/306; 206/366; 220/334, 338, 254, 259, 263, 351, 375, 324, 315, 314, 323, 906; 292/256.5

[56] References Cited

U.S. PATENT DOCUMENTS

| | | | |
|---|---|---|---|
| 2,831,595 | 4/1958 | Aspenes | 215/206 |
| 4,320,853 | 3/1982 | Moore | 220/375 |
| 4,502,606 | 3/1985 | Shillington et al. | 215/321 X |
| 4,723,673 | 2/1988 | Tartaglia et al. | 215/230 |
| 4,930,655 | 6/1990 | Wells | 220/375 X |
| 5,363,963 | 11/1994 | Allen | 220/324 X |
| 5,377,858 | 1/1995 | Morris, Sr. | 220/254 |
| 5,381,918 | 1/1995 | Dahl | 220/315 X |
| 5,439,130 | 8/1995 | Waugh | 220/315 X |
| 5,611,451 | 3/1997 | Mosior et al. | 220/254 X |

*Primary Examiner*—Gary E. Elkins
*Assistant Examiner*—Robin A. Hylton
*Attorney, Agent, or Firm*—Baker, Maxham, Jester & Meador

[57] ABSTRACT

A disposable container closure assembly, comprises a wall defining a circular opening for a substantially rigid container, a closure adapted to fit and close the opening, the closure having a first position for releasably engaging the wall and closing the opening, and a second position for engaging the wall and permanently closing the opening, and a flexible tether secured at a first end to the frame and detachably secured at a second end to the closure for retaining the closure in the first position, the tether being detachable from the closure for enabling positioning the closure in the second position.

17 Claims, 4 Drawing Sheets

CLOSURE FOR SHARPS DISPOSAL CONTAINER HAVING TEMPORARY AND PERMANENT CLOSED POSITIONS

BACKGROUND OF THE INVENTION

The present invention relates to sharps disposal containers, and pertains particularly to an improved closure having a temporary close position and a permanent close position.

The safe and efficient disposal of sharps such as surgical knives, blades, hypodermic needles and the like is a tremendous problem for medical and other healthcare facilities.

Disposable containers have been developed in recent years which provide a reasonably high degree of security for disposable sharps articles and materials from hospitals and clinics. Many of these articles, such as needles and surgical blades known as sharps, and other similar articles and materials, must be disposed of in a manner to keep them out of the hands of unauthorized persons and to keep them from being reused.

The containers are normally designed to prevent the removal of materials from the container under ordinary circumstances until permanently closed. The permanent closure is normally present on the container and often used as a temporary cover until the container is filled and ready for permanent closure. However the permanent closure is frequently unintentionally placed in the permanent position prior to completely filling the container. This results in unnecessary waste of containers and unnecessary cost. Therefore, it is desirable that the container be completely filled prior to permanent closure for disposal.

One secure container of the aforementioned type is that disclosed in prior U.S. Pat. No. 4,502,606, issued Mar. 5, 1985, and directed to a locking closure for disposable containers. These containers, have usually been provided with a permanent closure that is available to use as a temporary closure until ready for permanent closure. However, the closure is frequently mistakenly place in the permanent locking position prior to filling the container.

There is a need for a closure that may be safely used as a temporary closure without the danger of unintentionally placing it in the permanent closure position.

SUMMARY OF THE INVENTION

It is the primary object of the present invention to provide an improved closure that may be safely used as a temporary closure without the danger of unintentionally placing it in the permanent closure position.

In accordance with a primary aspect of the present invention, a disposable container closure assembly, comprises wall means for defining an opening for a substantially rigid container, a closure adapted to fit and close said opening, said closure having a first position for releasably engaging said wall means and closing said opening, and a second position for engaging said wall means and permanently closing said opening, and flexible tethering means secured at a first end to said frame means and detachably secured at a second end to said closure for retaining said closure in said first position, said tethering means being detachable from said closure for enabling positioning said closure in said second position.

BRIEF DESCRIPTION OF THE PREFERRED EMBODIMENTS

The above and other objects and advantages of the present invention will become apparent from the following description when read in conjunction with the accompanying drawings wherein.

DETAILED DESCRIPTION OF THE PREFERRED EMBODIMENTS

Figure 1:
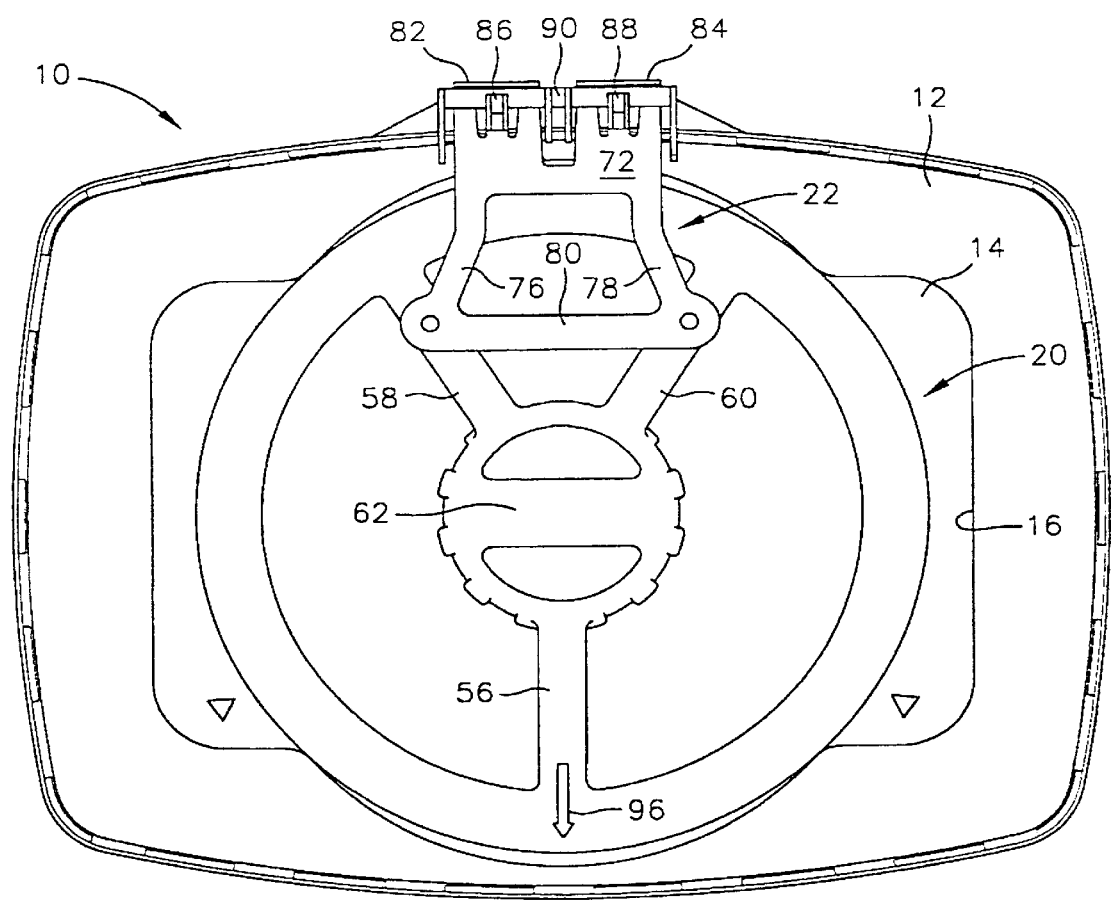
FIG. 1 is a top plan view of a closure assembly in accordance with a preferred embodiment of the invention.
Figure 2:
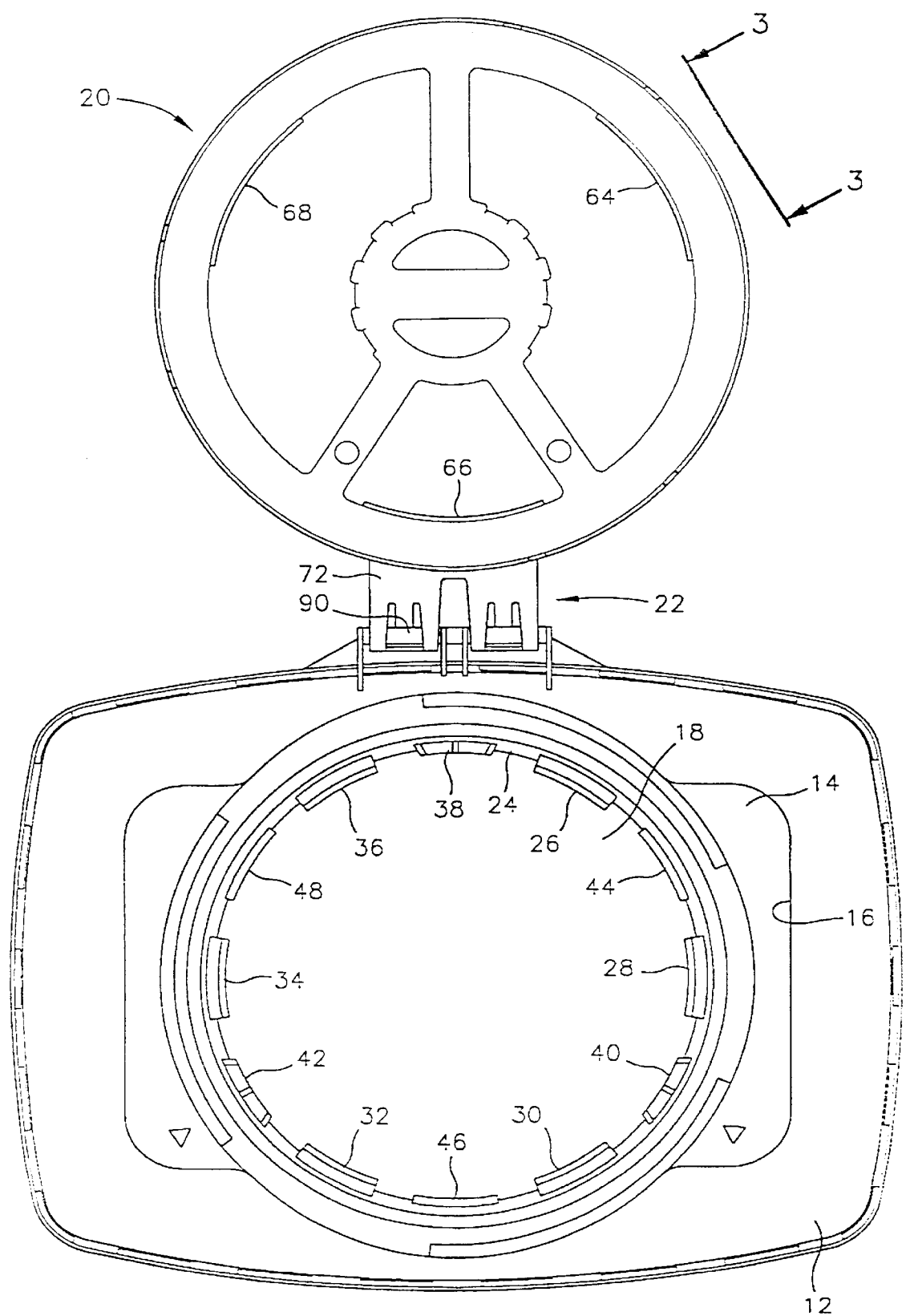
FIG. 2 is a top plan view like FIG. 1, showing the closure in the open position.

Referring now to the drawings and to particularly FIGS. 1 and 2, there is illustrated a top view of a container closure assembly, designated generally by the numeral 10, and comprises a closure frame 12 for mounting on an upwardly extending peripheral rim normally defining an upwardly directed opening of a substantially rigid container. The top support or frame member 12, in the illustrated embodiment has a generally rectangular configuration for mounting on and covering the upwardly opening mouth or open top of a container (not shown). This top is permanently attached to a plastic disposable container of the type typically used for the disposal of syringes, sharps and the like. These type containers are disclosed in a number of patents, such as mentioned above.

The frame or container top 12 has a central recess 14 formed with a downwardly depending wall 16 and with a circular opening 18 for receiving a circular closure member designated generally at 20. The closure member 20 is tethered or secured to the container by a hinge assembly or member designated generally at 22. The closure is designed to pivot or hinge about the side edge of the top frame or cover 12 to an open position, as seen in FIG. 2, to enable the insertion of articles to be disposed of into the container. The closure may then be swung down to the temporary closed position, as shown in FIG. 1, until time to insert other articles. At this time, the closure may be pulled up and swung over as shown in FIG. 2 to expose the opening for the insertion of articles. When the container is full, the closure is disconnected from the hinge member and then rotated 60° and pressed downward until it engages permanent latching means for permanently latching the closure into the opening. The container may then be disposed of in the usual manner.

Referring to FIG. 2, the container top or closure frame is molded of a thin sheet of plastic and has a recessed center portion 14, as shown, with a central circular opening 18 formed with a downwardly depending circular wall 24 having alternate guide and latching projections molded into it. As shown in FIG. 2 the wall defining the central circular opening, has six guide projections 26, 28, 30, 32, 34. and 36, extending outward toward the center of the opening from the wall. Disposed between alternate sets of the guide projections are temporary latch projections 38, 40 and 42. These projections have a substantially triangle or inverted V shape in side view. This provides a slope shaped upper and lower surface for detent-like temporary engagement with latch means on the closure, as will be described.

Also disposed between alternate pairs of the guide members are permanent latching members 44, 46 and 48. As will be appreciated, the permanent locking projections and the temporary locking projections are disposed at 60° intervals from one another about the axis along the periphery of the circular wall defining the opening. The permanent locking projections slope downward and outward to a lower straight horizontal surface that serves as a permanent latch for loops on the closure member, as will be described. The temporary latching members extend outward with an upwardly sloping lower surface for a detent like latching of the closure member in position.

Figure 3:
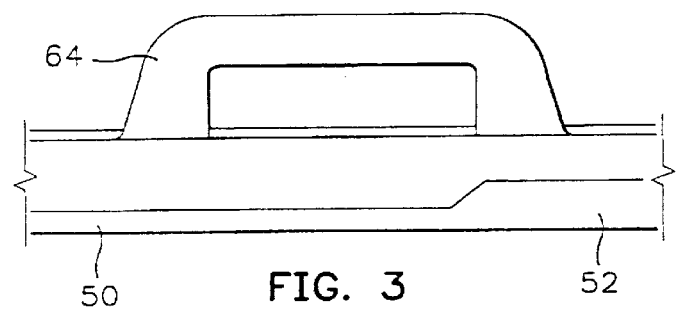
FIG. 3 is a view taken on line 3—3 of FIG. 2.

As will be appreciated from FIGS. 1, 2 and 3, the closure member 20 is molded of a thin sheet of circular plastic in the form of a peripheral or circular rim with a downturned lip 50 having extended projections 52 for reinforcement purposes. The center of the closure is recessed downward in semi-circular areas forming a central circular hub 54 with three radial ribs 56, 58 and 60 extending outward to the circular rim. A central transverse cross-bar 62 is formed in the central circular hub providing a hand grip. The central hub is molded with raised surfaces for reinforcement and to provide a grasping area.

Figure 5:
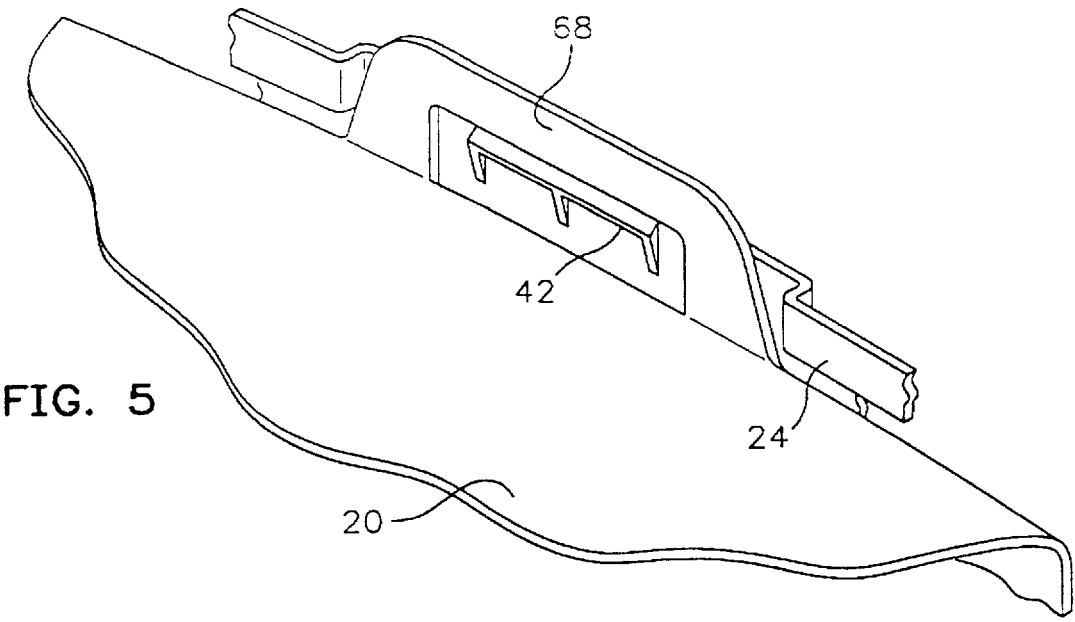
FIG. 5 is a perspective view showing details of the temporary latch.
Figure 6:
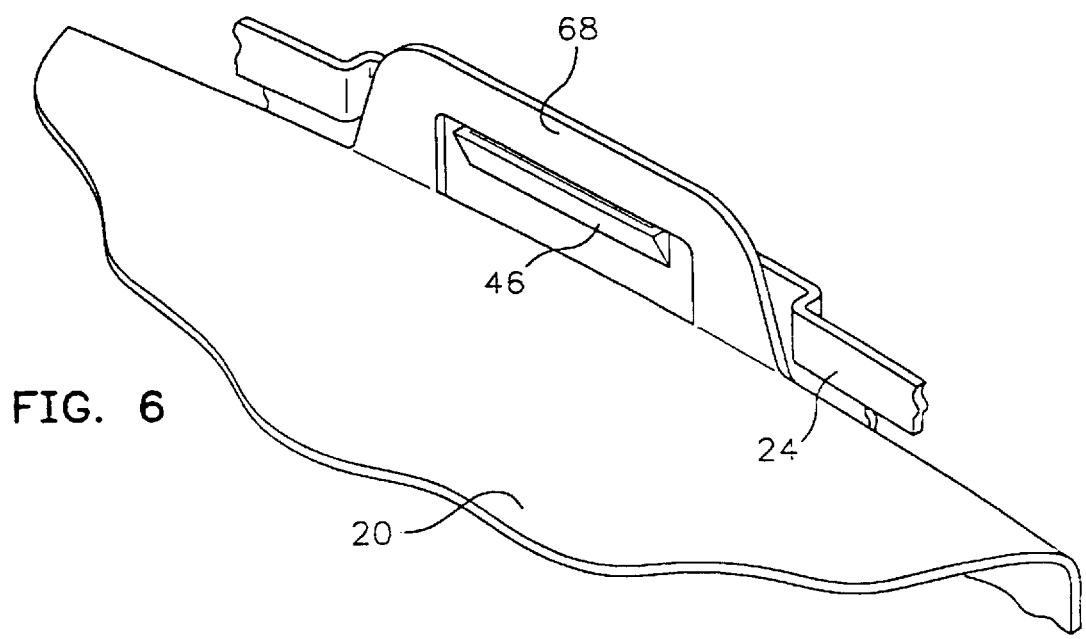
FIG. 6 is a perspective view showing details of the permanent latch.

The closure member is formed with three downwardly depending latching tabs having slots forming latching loops 64, 66 and 68. These latching loops extend downward from the peripheral edge of the depressed semi-circular areas on the underside of the closure. These latching loops are equally positioned around the circumference of the closure member to selectively register with and engage with the respective temporary and permanent latch projections, as shown in FIGS. 5 and 6. These latching loops 64, 66 and 68 are positioned to selectively engage the temporary latching projections 38, 40 and 42 (FIGS. 2 and 5) when the closure is in a first angular orientation about its center axis as seen in FIG. 1. The loops are positioned to engage the permanent latching projections 44, 46 and 48 (FIGS. 2 and 6) when the closure is in a second angular orientation about its axis as seen in FIG. 4.

A tethering or hinge member in the form of a generally rectangular open frame designated generally at 22 is hinged at one end to the closure frame 12 and detachably connected at the other to the closure. The hinge member 22 is formed with a central body 72 with arms 76 and 78 extending outward to and integral with a cross bar 80. A pair of generally cylindrical connector pins 82 and 84 are adapted to register with and frictionally engage a pair of sockets or bores 86 and 88 on ribs 58 and 60 on top of the closure to temporally connect them together in the position as shown in FIGS. I and 2. This is the temporary latching position of the closure as discussed above.

Figure 4:
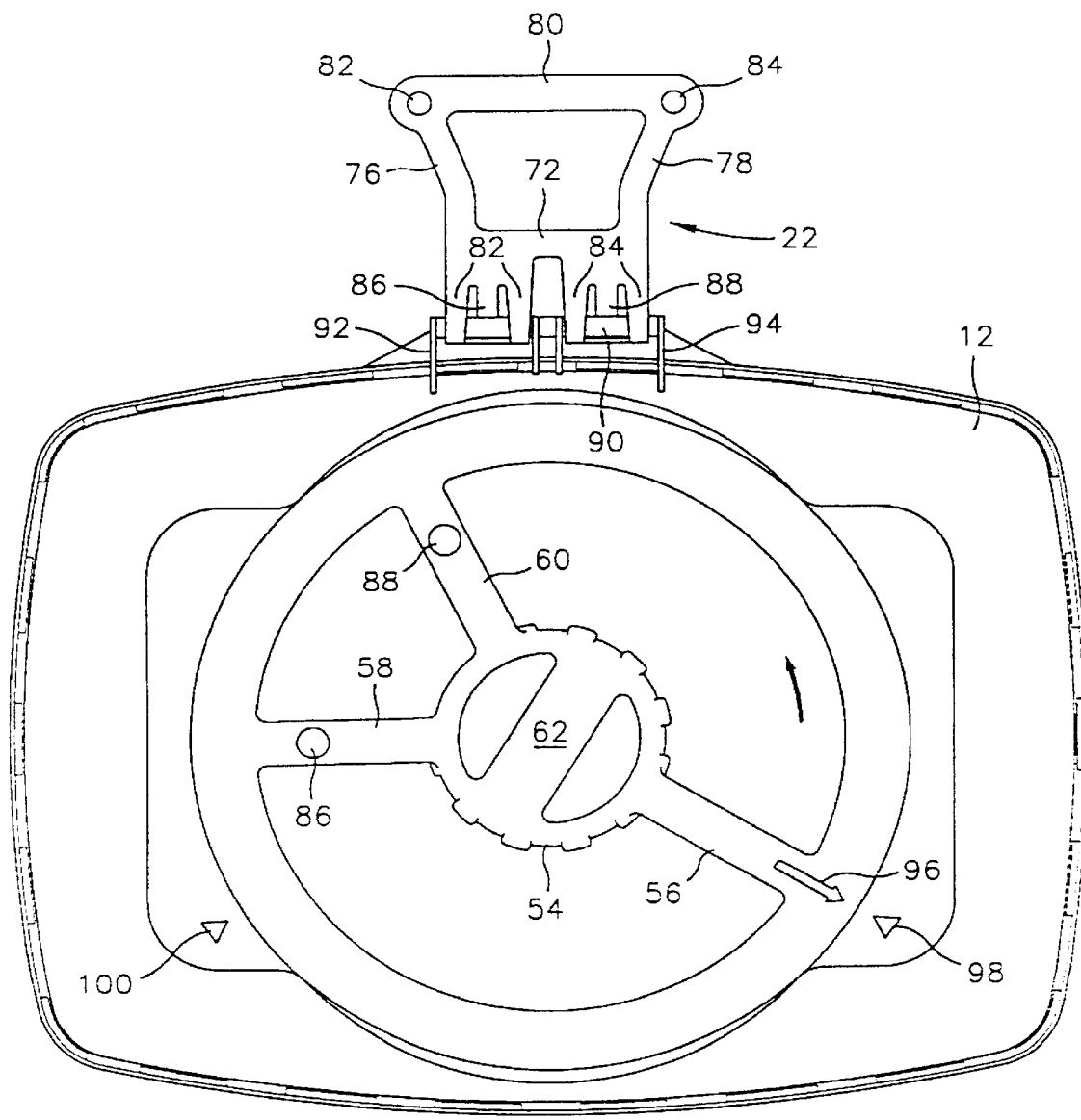
FIG. 4 is a top plan view like FIG. 1, showing the closure in the permanent closed position.

The pins of the hinge are removable from the sockets as shown in FIG. 4. to enable the closure to be rotated to the permanent latching position. This pin and socket combination temporarily connects the closure to the hinge or tethering member which is hinged to the side of the closure frame. The hinge member is formed with closing hooks 82 and 84 and shoulders 86 and 88 which engage a transverse pivot pin or rod 90 formed with stand-off arms 92 and 94 as a bracket on the rim of the closure frame. When the closure is secured to the hinge member as shown in FIGS. 1 and 2, the orientation is such that the latch tabs orient with and engage the temporary latching projections as shown in FIG. 5. This enables the closure to be positioned and fixed in that position by the hinge to enable one to temporarily close the opening in the container and to later open it for the insertion of disposable items.

The closure is provided with indicia means in the form of an arrow 96 on a top portion thereof opposite the hinge and small diamond shaped or triangle shaped markers 98 and 100 molded into the top of the closure frame. When these are properly oriented, the closure may be pressed down into its permanently locked or latched position. The container is then ready for total disposal as in the usual manner.

As shown in FIG. 1, the closure is formed with indicia means in the form of an arrow 96 on top of rib 56 which points straight ahead in the temporary close position. The hinge 22 maintains the closure in its orientation as long as it is connected as illustrated.

Once the container is completely filled, the closure member may be disconnected from the orienting tether or hinge 22 member by simply grasping and pulling up on the bar 80 between the pins of the hinge member removing the pins from the sockets in the top of the closure member. The closure member may then be lifted and rotated 60° orienting the arrow 96 with indicia in the form of triangles 98 and 100 on the closure frame and pressed down to a permanent latching position.

While I have illustrated and described my invention by means of specific embodiments, it is to be understood that numerous changes and modifications may be made therein without departing from the spirit and scope of the invention as defined in the appended claims.

I claim:

1. A disposable container closure assembly, comprising:
    wall means for defining an opening for a substantially rigid container;
    a closure adapted to fit and close said opening, said closure having a first position for releasably engaging said wall means and closing said opening, and a second position for engaging said wall means and permanently closing said opening; and
    hinge means secured at a first end to said wall means and detachably secured at a second end to said closure for retaining said closure in said first position, said hinge means being detachable from said closure for enabling positioning said closure in said second position.

2. A closure assembly according to claim 1 wherein said opening is circular and said closure is circular.

3. A closure assembly according to claim 2 wherein said closure includes first latch means, and said wall means includes second latch means, and said first latch means and said second latch means engage when said closure is in said second position.

4. A closure assembly according to claim 1 wherein said wall means includes projections, and said closure includes loops, and said loops loop over said projections when said closure is in said second position.

5. A closure assembly according to claim 1 wherein said wall means defining said opening is circular having a top edge and a lower edge, hook means formed on said lower edge, and said closure is circular having loop means for engaging said hook means when in said second position.

6. A closure assembly according to claim 1 wherein:
    said wall means is a closure frame for a disposable container;
    first locking means on one of said wall means and closure means; and
    second locking means on the other of said wall means and closure means, said first and second locking means engaging for permanently locking said closure means in said opening when in said second position.

7. A closure assembly according to claim 6 wherein:
    one of said first and second locking means comprises a hook; and
    the other of said locking means comprises a loop for engagement with said hook.

8. A closure assembly according to claim 7 wherein:

said opening and said closure are circular; and said hinge means comprises a rectangular open frame secured by a hinge at said first end to said frame, and secured by a pair of spaced apart pins and sockets at said second end to said closure.

9. A closure assembly according to claim 7 further comprising indicia means on said closure frame wall means and on said closure for indicating said second position.

10. A closure assembly according to claim 1 further comprising indicia means on said closure frame wall means and on said closure for indicating said second position.

11. A closure assembly for a disposable container, comprising:

closure frame means for mounting on an upwardly extending opening defining a peripheral rim of a substantially rigid container;

an opening in said frame means for receiving an article;

a closure having a first position for releasably engaging and closing said opening, and a second position for engaging and permanently closing said opening; and a hinge member pivotally connected at one end to said frame means and detachably secured at another end to said closure for retaining said closure in said first position, said hinge member being detachable from said closure for enabling positioning said closure in said second position.

12. A closure assembly according to claim 11 wherein:

said opening is circular and said closure is circular; and said closure includes first latch means, and said wall means includes second latch means, and said first latch means and said second latch means engage when said closure is in said second position.

13. A closure assembly according to claim 12 wherein said first latch means comprises loops, and said second latch means comprises projections, and said loops loop over said projections when said closure is in said second position.

14. A closure assembly according to claim 11 wherein said wall means defining said opening is circular having an upper edge and a lower edge, hook means formed on said lower edge, and said closure is circular having loop means for engaging said hook means when in said second position.

15. A closure assembly according to claim 14 further comprising indicia means on said closure frame wall means and on said closure for indicating said second position.

16. A closure assembly according to claim 15 wherein said closure has a plurality of downward depending tabs having slots defining said loops, a plurality of stiffening ribs extending radially from a center thereof, and sockets in a pair of said ribs for receiving pins on said hinge member for detachably attaching said hinge member to said closure.

17. A closure assembly according to claim 10 wherein said wall comprises sloped projections for engagement by said loops in said first position, and a non-sloped shoulder for engagement in said latched position.

\* \* \* \* \*